Figure 1:
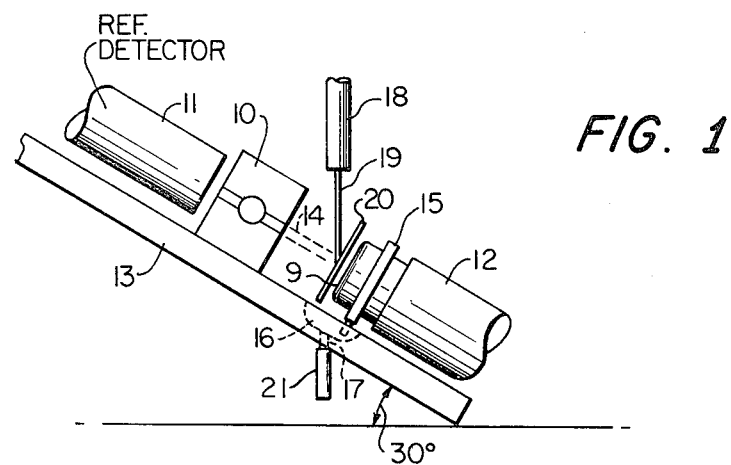

United States Patent [19]

Lawson et al.

[11] 4,275,304
[45] Jun. 23, 1981

[54] SHORT OPTICAL PATH DETECTOR

[75] Inventors: Alexander E. Lawson, Mendham; Robert J. Mathieu, Mountain Lakes; James M. Miller, Madison, all of N.J.

[73] Assignee: GOW-MAC Instrument Co., Bound Brook, N.J.

[21] Appl. No.: 72,685

[22] Filed: Sep. 5, 1979

Related U.S. Application Data

[63] Continuation of Ser. No. 893,406, Apr. 4, 1978, abandoned.

[51] Int. Cl.³ .............................................. G01J 1/42
[52] U.S. Cl. .................................. 250/373; 250/434; 356/410
[58] Field of Search .................. 250/304, 343, 358 R, 250/359, 373, 432 R, 434; 118/636; 356/70, 409, 410

[56] References Cited

U.S. PATENT DOCUMENTS

| 2,091,222 | 8/1937 | Thomas | 356/70 X |
| 2,971,461 | 2/1961 | Bradford et al. | 250/359 X |
| 3,980,882 | 9/1976 | Carr-Brion et al. | 250/358 R X |
| 4,027,983 | 6/1977 | Abrahams | 250/373 X |

Primary Examiner—Davis L. Willis
Attorney, Agent, or Firm—Fidelman, Wolffe & Waldron

[57] ABSTRACT

An improvement in analytic instruments which measure liquid properties by optical techniques, the improvement providing an optical path through the liquid under test as low as about 0.1 mm by presence of a flat transparent surface across the optical beam and by flowing a film of the liquid under test down the surface, the depth of the film being the optical path through the liquid.

Desirably the surface is normal to the beam, but at an acute angle to horizontal. A matted surface is desirable for spreading high viscosity solvents across the surface.

7 Claims, 2 Drawing Figures

SHORT OPTICAL PATH DETECTOR

This is a continuation, of application Ser. No. 893,406, filed Apr. 4, 1978, now abandoned.

This invention relates to analytic instruments which measure liquid properties by optical techniques and briefly is an improvement directed to provision of a short optical path through the liquid test sample within an optical instrument adapted for analysis of a liquid sample such as for example the UV detector of a liquid chromatography system.

BACKGROUND OF THE INVENTION

A great number of analytic instruments based upon the optical properties of a liquid sample have been proposed to the arts. In common such instruments provide an optically transparent path for the beam from an emitter of the radiation to a receptor. The liquid sample to be analyzed is interposed across the beam so that the radiation received by the receptor has been altered (in some optical sense) by interposition of an optical path through the liquid sample. Typically the optical system employs infrared, visible or ultraviolet radiation and measures optic changes caused by passage through the liquid, e.g. the degree to which monochromatic ultraviolet light has been absorbed by the sample. One notable and widely used optical system measures UV absorption of the 254 nm mercury line, by the sample. Another notable optical system provides detection in the infrared region of the spectra of the sample. Still other optical systems employ polarimetry, refractive index, turbidimetry (nephelometry) or fluorimetry for analytic purposes.

The present invention can be employed in the optical path of any optical technique instrument wherein the least length optical path through a liquid is desirable. For each of discussion, this invention will be described in detail in terms of use within the context of liquid chromatography with a UV detector system (a preferred embodiment).

As is well known to the art (see "Introduction of Modern Liquid Chromatography" by R. L. Snyder and J. J. Kirkland; John Wiley & Sons, 1974) liquid chromatography involves chromatographic separation of a test sample in a liquid moving phase by adsorption, partition or ion exchange, typically in a column. The chromatographed solution is then analyzed by measuring absorption of ultraviolet light in the chromatographed liquid as the UV traverses the optical path therethrough.

The laws of Absorption in Spectroscopy state that the fractional part of the monochromatic radiant energy, or intensity, absorbed in a thin layer of material depend upon the substance and upon the frequency of the incident radiation and is proportional to the thickness, i.e. Beer's Law:

$$A = \epsilon b c$$

where $A$ = absorbance, $\epsilon$ = molar absorptivity, $b$ = cell (or path) length in cm, and $c$ = concentration in moles/L. Further, absorbance is defined relative to the incident radiant energy, $P_o$ and the transmitted energy, $P$, as:

$$A = \log_{10} \frac{P_o}{P} = \log\left(\frac{1}{T}\right) \text{ and } T = \text{transmittance} = \frac{P}{P_o}$$

Materials which have a large absorbance value, e.g. long conjugated molecules, particularly in high concentration, are difficult to analyze with standard spectrophotometers due to the large extinction coefficients (molar absorptivity), i.e. the point at which the light passing through the sample is effectively extinguished.

In liquid chromatographic detection, as in normal absorption spectroscopy, the common optical path length is 10 mm. In preparative LC work, the samples get rather large and thus the concentration of highly absorptive substance in the detector are high. The result is excessively large absorbance values. If, for example, the molar absorptivity, $\epsilon$, of an LC sample is 3,000 (a typical, high value), and if the concentration in the detector attains a maximum value of $7 \times 10^{-3}$ M, and a 1.0 cm cell is used, the absorbance calculates out to:

$$A = (3 \times 10^3)(7 \times 10^3)(1.0)$$
$$= 21$$

Such a value, (21), is much too high for most spectrophotometers. Detectors in LC systems respond to changes in concentration of the sample substance in the solvent. Within instrument limits such response is linear, i.e. straight line. Suffice is here to merely point out that the linear response is proportional to the size of the various samples intended for the LC system, and the linear response is plotted as a straight line. However, at some concentration of the sample substance in the solvent all detectors respond in a non-linear manner. A detector is considered overloaded when additional quantities of (a pure) sample no longer result in an increased response or signal. Since the typical LC system exhibits a linear response only up to about 2.0 A, the value of 21 calculated out above is very much of an overload.

Analytic instruments employing an optical characteristic for measurement purposes have included heretofore a closed chamber or cell formed from materials transparent to the radiation employed (e.g. glass, quartz) positioned across the beam of radiation inside the instrument. The chromatographed solution is, of course, passed through the cell, and the cell dimensions are what fix the optical path length, (e.g. thickness "b" for absorptivity measurement). The usual cell length is 2-10 mm. The nature of liquid flow through capillary sized channels preclude substantial reduction in cell dimensions e.g. to below about 1 mm. Moreover, accurately dimensioned short optical path cells of below about 1 mm would be quite expensive to fabricate.

None the less an optical path (length "b") of very small dimensions would be advantageous for optical measurements on materials with very large molar absorptivity values and/or high concentration levels. If the path length is reduced to 0.1 cm (1 mm) the absorbance calculated above decreases to 2.1, a value reasonable for most spectrophotometers. A further decrease in path length to 0.01 cm (0.1 mm) would reduce the absorbance to 0.21, which is a very low value.

Thus, by a substantial reduction in the length of the optical path, the A (Absorbance) is lowered significantly. High absorbancy samples cain be held to the range of linearity of existing UV detectors (about 0.001 A to 2.0 A). an optical path of about 0.1 mm, a path length desired for analyzing samples with high absorbance, may be attained by practice of this invention.

STATEMENT OF THE INVENTION

Briefly stated the present invention substitutes a flowing film of liquid for the liquid filled cell heretofore employed for the optical path in optical analytic instruments.

A surface transparent to the radiation in the instruments disposed across the beam and delivery means are present to spread the liquid sample on the surface as a flowing film thereon. Liquid film thicknesses of about 0.1 mm are routinely obtainable.

RATIONALE OF THE INVENTION

The scientific basis for practice of this invention is that the film thickness of laminar flow liquid films on a flat surface is about 0.1–0.2 mm. Such films can be reliably reproduced time and again. Moreover the characteristics of falling liquid films constitute well explored scientific phenomena. For example, "Perry's Chemical Engineer's Handbook" McGraw-Hill, N.Y. 5th Ed. Sec. 5 page 57 contains a summary of the theoretical equations describing laminar flow of liquid films down flat surfaces.

Assuming no surface attractive forces, an equation of interest to practice of this invention is:

$$m = \text{film thickness in cm} = \left[ \frac{3 L \mu}{g D_f(D_f - D_c) \sin \phi} \right]^{\frac{1}{3}}$$

where:
- L = liquid loading per unit width of plate (g sec$^{-1}$ cm$^{-1}$)
- u = viscosity (poise or g sec$^{-1}$ cm$^{-1}$)
- g = acceleration of gravity = 980.7 cm sec$^{-2}$
- $D_f$ = density of fluid (g cm$^{-3}$)
- $D_c$ = density of surrounding fluid (g cm$^{-3}$).
- $\phi$ = angle of inclination with the horizontal Normally the surrounding fluid would be air for which $D_c \sim 1.2 \times 10^{-3}$ g/cm$^3$, a value which is negligible compared to $D_f$, the density of the liquid sample.

An exemplary sample calculation, adequate for an approximation of the film thickness to be expected can be made by assuming the liquid to be one of the solvents conventionally employed in liquid chromatography, e.g. n-hexane, and a liquid flow rate corresponding to some typical flow rate employed in preparatory chromatographic columns e.g. 10 ml per minute. Arbitrarily assumed are a 90° inclination to horizontal, and a falling film width of 1 cm for computation of L. Then:

$L = 10$ ml/min $\times 0.66$ g/ml $\times 1/60$ sec/min $\times 1/1$ cm $= 0.11$ g sec$^{-1}$ cm$^{-1}$ $\mu = 3.26 \times 10^{-3}$ poise $D_f = 0.66$ g cm$^{-3}$ and $(D_f - D_c) = D_f$ $$m = \left( \frac{3 L \mu}{g D_f^2 \sin \phi} \right)^{\frac{1}{3}} = \left( \frac{3 \times .11 \times 3.26 \times 10^{-3}}{980.7 \times (.66)^2 \times 1} \right)^{\frac{1}{3}}$$

$= (2.52 \times 10^{-6})^{\frac{1}{3}} = 0.014$ cm $= 0.14$ mm

The 0.1–0.2 mm range for thickness predicted by the above computation has been confirmed experimentally. Apparently the physical factors ignored in the above equation such as surface tension, wetting angle etc. are not of major consequence to film thickness, affecting it is believed mostly the width attained by the (unconfined) falling film.

As described in more detail hereinafter, laboratory tests wherein a preferred mode of falling film optical path was substituted in a standard UV detector (for the 10 mm cell) demonstrated that film flow down a flat surface is sufficiently stable and reproducible for measurement of UV absorption therein, i.e. the falling film can be the optical path of a liquid sample.

Thus falling film theory, experimentally confirmed, indicate that a falling film can provide the short optical path desired for analytic optical instruments.

The experimental work in confirmation of falling film theory indicated the desirability of certain practical expedients worthy of note.

Thus, it was found desirable to vary circumstances of the falling film away from the assumptions made for the above falling film computation. Specifically, a less than 90° angle of the surface to horizontal improved coherency of the falling film, an acute angle should be employed, 60°–75° being preferred.

Even when the surface on which the liquid is applied is canted, film spread was less than expected. No matter how the needle feeding the liquid was angled to the surface or shaped, solvents with a relatively high viscosity would not spread over the sample plate. However, when the surface was sand blasted to a matte finish (or ground finish, or etched finish), the liquid spread well. It seemed that liquids with viscosities exceeding 0.386 poise required the matte finish.

The manner that the liquid is fed on to the surface had some affect on the film, particularly with regard to formation of waves or ripples in the film. The standard 12° point needle used in medical syringes seemed to perform best at a variety of interface (to the surface) angles and the flow rates. For flow rates up to 20 ml/minute a 20 gauge needle yielded smooth flow.

DISCUSSION OF THE INVENTION

Application of a falling film optical path to optical instruments according to one preferred mode of practice of this invention is in the form of a plug-in detector accessory to existing analytic systems that produce a liquid sample solution for an optical measurement such as, for example, a liquid chromatography column. Basically the accessory contains the radiation emitter and receptor, and the transparent surface disposed across the beam path from emitter to receptor. Associated with the transparent surface are means for flowing sample liquid to the top of the surface and means for collecting the liquid from the bottom of the surface. Desirably the surface is matted to a ground glass finish (to assist in spreading a uniform film) and desirably also the surface is normal (i.e. at 90°) to the optical path, but the entire optical path is canted relative to horizontal, e.g. at 30° to horizontal so that the surface over which the liquid flows is at an acute angle (also to assist in spreading a uniform film).

In keeping with the accessory concept, the sample receiving and discharging elements present are adapted to attach to already existing inlets and outlets present in conventional optical instrument systems, and the receptor (which, per se, may well be a duplicate of the receptor already in the instrument system) plugs into whatever read-out is in the instrument system. The emitter will of course be plugged into the existing power supply in the instrument system. Contemplated in the accessory are means for (optionally) positioning one or more neutral density filters across the beam path. The short optical paths obtained by practice of this invention will often allow excessive transmission of radiation (e.g. UV) to the receptor and filters will be required.

The falling film optical path herein contemplated will, of course, have characteristics somewhat different from the characteristics of the optical paths heretofore used by the art. For example, the sample cells employed in ultra violet light absorption detectors are of known dimensions, and are sealed (from air). In contrast the falling film is unconfined, it has a liquid-gas (i.e. air) interface, and it will vary in thickness liquid to liquid according to differences in viscosity, wetting angle, surface tension etc. Some of the variability liquid to liquid attributable to differences in wetting angle and surface tension can be minimized by employing a relatively small diameter beam positioned centrally of the film. The extent of the film spread over the surface will depend on the physical properties of the liquid, but at its center the film has an almost flat gas-liquid interface and a reasonably uniform thickness. That portion of the film within the beam will be uniform in thickness, but to repeat will vary in thickness, liquid to liquid in proportion to $\mu^{\frac{1}{2}}$.

In passing it may be noted that the liquid sample must be stable to air or an inert atmosphere e.g., no precipitation of solids, no chemical reactions.

With regard to use of the falling film optical path in measurement of ultra-violet light absorption by the sample, the major difference in read-out resulting from variations in film thickness due to uneven film flow is in the "noise" level (i.e. random fluctuations in the base line reading and in the absorbance curve line). The major difference caused by a high viscosity solvent vs. low viscosity solvent is in the amplitude of the absorption curve. (Which should be expected since high viscosity solvents have the longer optical path). Standardizing the instrument system against known solutions of solvent and of test material may be advisable.

The accessory for existing instrument systems as has been described above is but one preferred mode of this invention. Manifestly, an entire instrument system may be built around the falling film optical path.

DETAILED PRACTICE OF THE INVENTION

Figure 2:
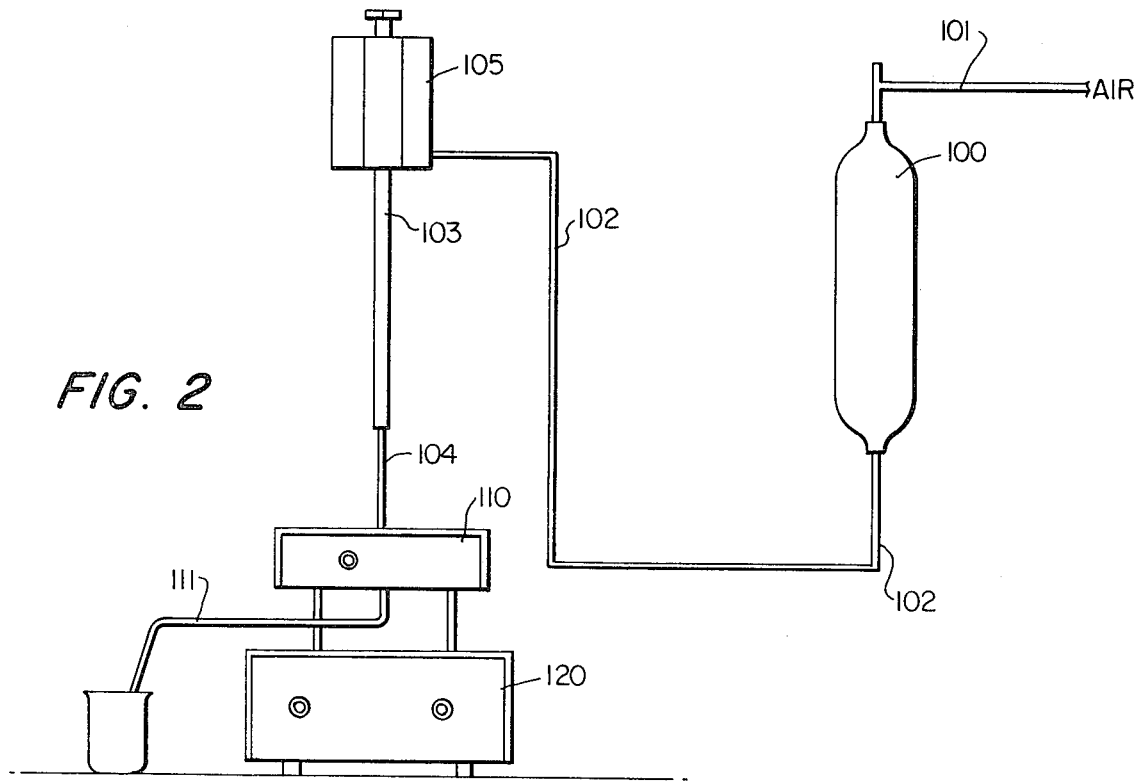

For further understanding of this invention reference is made to the attached drawing wherein;

FIG. 1 illustrates the falling film optical accessory in an unhoused configuration assembled on an optical bench, and FIG. 2 illustrates the falling film optical path as part of a liquid chromatography with UV detector instrument system.

Referring now to FIG. 1 wherein is illustrated an optical path through a falling film associated with a UV emitter and detector. The emitter 10, a reference detector 11 and absorption detector sensor 12 are mouned on optical bench 13 so that the beam 14 from emitter 10 to detector 12 are in alignment. It may be noted that bench 13 is canted 30° from horizontal, which in turn cants the (quartz) face of detector 12 60° from horizontal. The liquid from needle 19 passes over the quartz plate 20 which, preferably has a matte surface thereon.

In the (experimental purposes) mode of FIG. 1, enough of the housing around a phototube was stripped to allow access to the front face of the tube, and to allow placement of a collar 15 around the tube. In addition a well 16 and aperture 17 were drilled through optical bench 13.

The sample containing solution from some suitable source, e.g. chromatographic column 18 feeds into a tube (e.g. needle) 19 that terminates flush agains the flat surface face 20 mounted on detector 12. The solution leaving needle 19 flows as a falling film down surface 20, then drains into well 16, and out of the accessory by way of aperture 17 and drain line 21. The 60° angle of surface 20 and the matte or ground glass finish placed thereon for use with viscous solvents create smooth film flow. At the usual rates of flow from a preparatory chromatographic columns, e.g. 10 ml/min, the film does not spread across the entire face of plate 20, a desirable consequence because unconfined flow of the liquid creates the thinnest films.

Since the operation of reference emitter 10, detector 12 reference detector 11, etc., including the electrical connections for measurement of UV absorbence are well known to the art the details thereof have not been illustrated. Suffice it simply to note that customary practices with regard to such details are herein contemplated. (It may, however, be noteworthy) that interposition of several neutral density filters in beam 14 were required to weaken the UV absorbency signals sufficiently to keep the signal on scale and to permit calibration of the accessory with a standard recorder).

FIG. 2 illustrates how the falling film optical path arrangement of the present invention may be incorporated into an overall analytic instrument system, namely into a typical liquid chromatograph with UV detector.

As may be seen in FIG. 2 the typical liquid chromatography instrument schematically shown thereon comprises a solvent source, and constant pressure pump powered by (cylinder) air or nitrogen from line 101. The carrier liquid passes from assembly 100 by way of line 102 to the entrance of chromatography column 103. The test sample is introduced into column 103 through injection port 105. Chromatographed liquid leaving column 103 through outlet line 104 passes to the short path UV detector 110. The short path UV detector 104, is of course constructed as has been described, and indeed, could be exactly as shown in FIG. 1, but preferably is modified for good manufacturing and shipping practices. For example stripping shielding from an existing phototube is a suitable way to produce a laboratory experimentation detector, but in mass manufacturing practice a separate (quartz) sheet would be matted to a ground glass finish and then securely mounted in front of the phototube. In addition, the optical bench 13 might well be replaced (e.g. by a rear side support) to leave the underside of the sheet free for placement of a cup and drain line to catch and remove solvent solution from short path UV detector 110. In any event the solution of chromatographically separated sample is analyzed optically by UV absorbance in detector 110 then discarded to a collector by way of line 111. While control unit 120 is illustrated, the recorder which forms part of the analytic system is not shown.

For further understanding of the practice of this invention, the following examples are presented.

EXAMPLE I

The multiplicity of solvents were tested for falling film characteristics by passing a representative group of solvents through a 20 gauge surgical needle at 10 ml/min on to a flat quartz surface and on to a sand blasted quartz surface. The plate was 60° to the horizontal. The width of the liquid stream was measured (inches). The results are tabulated below:

| MATERIAL TESTED | VISCOSITY | Flat A | Matte B |
| --- | --- | --- | --- |
| Isooctane | .237 | ¾ | ¾ |
| Hexane | .294 | 1 | 1 |
| Acetone | .316 | 1 | 1 |
| Acetonitrile | .345 | ¾ | ¾ |
| Heptane | .386 | 1 | 1 |
| Ethyl Acetate | .441 | ¾ | 1 |
| Cyclopentane | .493 | ⅝ | 1 |
| Chloroform | .542 | ½ | ¾ |
| Methanol | .547 | ¾ | 1 |
| Ethylene Chloride | .800 | ½ | ¾ |
| Water | .89 | ½ | ½ |
| Carbon Tetrachloride | .906 | ¼ | ¾ |
| Isopropanol | 1.77 | ¼ | ¾ |
| Propanol | 1.98 | ¼ | ¾ |

EXAMPLE II

Measurement of optical path in Short Path Length Detector

A 300 ml solution of 1.0 mg/ml napthalene in isooctane was pumped through a silica gel column 10 cm × 1 cm dia. at a flow rate of 10.3 ml/min. The sample was eluted into the SPLD. A recorder deflection was 209 mm at attenuation of 0.32 A.U.F.S. (absorbance units full scale). Recorder full scale equals 250 mm Using Beer's Law (A=Ebc) and solving for the path length (b) under the test conditions of E=4000 for naphthalene, C=0.0078 moles/L and A=0.2675 (which is 0.32×209/250), the path length calculates out to 0.086 mm, a value in agreement with falling film theory.

The short optical path surface was a sand blasted quartz plate disposed at 60°, fed through a 20 gauge surgical needle.

EXAMPLE III

A commercial Liquid Chromatograph with UV detector (Series 80-500 GOW MAC Instrument Co.) was employed for the tests of this example, with the standard 10 mm path length cell, then with the cell replaced by a sand blasted quartz plate disposed at 60° fed through a 20 ga surgical needle.

The sample used was cumene (isopropyl benzene) in isooctane and isooctane was the mobile phase. Sample concentration was 810 mg/ml. The sample was injected in increasing amounts 1 µl, 2 µl, 10 µl; an overload condition was exhibited at 1.62 mg cumene (2 µl injection).

The TFD (thin film detector) 0.1 mm path length, was then attached to the same column and the experiment was repeated as on the 10 mm path length detector. The TFD showed an overload condition at 162 mg cumeme (200 µl injection) which is a factor of 100 greater concentration.

The results of this test demonstrate the application of the TFD to analysis of compounds that are very concentrated and or exhibit large molar absorptivity in the UV range.

What is claimed is:

1. In an optical technique analytic instrument system wherein a liquid test sample is flowed through an optical path crossed by a beam, the improvement which comprises a flat surface disposed across the beam and at an acute angle to horizontal, said surface being transparent to the beam, and sample delivery means flush to said surface for flowing an unconfined falling film of a partially transparent liquid test sample over said surface, the falling film of liquid test sample on said surface constituting the analytic instrument optical path through the liquid test sample.

2. The apparatus of claim 1 wherein the flat surface is perpendicular to the optical path and the film is not more than about 0.2 mm thick.

3. The apparatus of claim 2 wherein the acute angle is 60°-75°.

4. The apparatus of claim 1 wherein the flat surface has thereon a matte finish.

5. A liquid chromatography analytic instrument comprising:
   (a) separator means for chromatographically separating the components of a test sample dissolved in a carrier liquid;
   (b) an ultra violet light detector for analyzing the UV absorbance of the solution, said detector including therein a beam of ultra-violet radiation and a surface disposed across the beam and at an acute angle to horizontal, said surface being transparent to the beam;
   (c) means for passing test sample in solvent solution through the separator, and means for introducing solution from the separator into said detector the latter means including sample delivery means flush to said surface for flowing an unconfined film of chromatographed solution over said surface, the film of chromatographed solution on said surface constituting the optical path through the separated solution, and
   (d) means for removing liquid flowing off said surface and from said detector.

6. The analytic instrument of claim 5 wherein the flat surface is perpendicular to the optical path and the film is not more than about 0.2 mm thick.

7. The analytic instrument of claim 5 wherein the flat surface has thereon a matte finish.

* * * * *